United States Patent
Johnson et al.

(10) Patent No.: US 7,439,244 B2
(45) Date of Patent: Oct. 21, 2008

(54) QUINOLINE COMPOUNDS AND PHARMECEUTICAL COMPOSITIONS CONTAINING THEM

(75) Inventors: Christopher Norbert Johnson, Harlow (GB); David R Witty, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 159 days.

(21) Appl. No.: 10/571,405

(22) PCT Filed: Sep. 9, 2004

(86) PCT No.: PCT/EP2004/010129

§ 371 (c)(1), (2), (4) Date: Mar. 10, 2006

(87) PCT Pub. No.: WO2005/026125

PCT Pub. Date: Mar. 24, 2005

(65) Prior Publication Data

US 2006/0287334 A1   Dec. 21, 2006

(30) Foreign Application Priority Data

Sep. 12, 2003   (GB) ................. 0321473.1

(51) Int. Cl.
 *A61K 31/496* (2006.01)
 *A61K 31/551* (2006.01)
 *C07D 215/40* (2006.01)
(52) U.S. Cl. ............. 514/253.07; 514/218; 540/575; 544/363
(58) Field of Classification Search ............ None
 See application file for complete search history.

(56) References Cited

U.S. PATENT DOCUMENTS 6,251,893 B1   6/2001   Slassi et al. ............ 514/214.01

FOREIGN PATENT DOCUMENTS

| WO | WO 00/42026 A1 | 7/2000 |
|---|---|---|
| WO | WO 00/63203 A1 | 10/2000 |
| WO | WO 02/100822 A1 | 12/2002 |
| WO | WO 03/035061 A1 | 5/2003 |
| WO | WO 03/037871 A1 | 5/2003 |
| WO | WO 03/037872 A | 5/2003 |
| WO | WO 03/042208 A1 | 5/2003 |
| WO | WO 03/080580 A2 | 10/2003 |

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Bromidge et al. Bioorganic & Medicinal Chemistry Letters, vol. 11, p. 55-58 (2001).*
Ahmed et al. Bioorganic & Medicinal Chemistry Letters vol. 15, p. 4867-4871 (2005).*
U.S. Appl. No. 10/509,078 filed Sep. 27, 2004, Ahmend et al.*
Heal et al. Pharmacology & Therapeutics, vol. 117, p. 207-231 (2008).*
Wooley et al. *Neuropharmacology*, vol. 41: 210-219 (2001).
Mitchell et al., *Pharmacol. & Therapeutics*, 108: 320-333 (2005).
Chuang et al., *Alzheimer's & Dementia, The Journal of the Alzheimer's Association*, 2(3/Supp. 1): S631-S632 (2006).
London Stock Exchange Announcement—GlaxoSmithKline (GSK) plc, Issued on Thursday, Dec. 13, 2007, New York, New York.
A Dose Ranging Study to Investigate the Efficacy and Safety of SB-742457 in Alzheimer'Disease. NCT ID No. NCT00224497 (Verified 2007).
SB-742457 and Donepezil in Alzheimer's Disease. NCT ID No. NCT00348192 (2006).
Garcia-Alloza et al. *Neuropsychopharmacology*, 29: 410-416 (2004).

* cited by examiner

*Primary Examiner*—Emily Bernhardt
(74) *Attorney, Agent, or Firm*—Kathryn L. Sieburth; Mary E. McCarthy; Charles M. Kinzig

(57) ABSTRACT

Disclosed are quinoline compounds of formula (I) having pharmacological activity, processes for their preparation, compositions containing them, and methods for the treatment of CNS and other disorders.

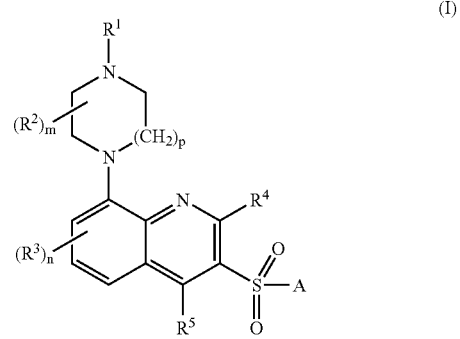

13 Claims, No Drawings

QUINOLINE COMPOUNDS AND PHARMECEUTICAL COMPOSITIONS CONTAINING THEM

This invention relates to novel quinoline compounds having pharmacological activity, to processes for their preparation, to compositions containing them and to their use in the treatment of CNS and other disorders.

JP 02262627 (Japan Synthetic Rubber Co) describes a series of substituted quinoline derivatives useful as wavelength converting elements. WO 00/42026 (Novo Nordisk) describes a series of quinoline and quinoxaline compounds for use as GLP-1 agonists.

A structurally novel class of compounds has now been found which also possess affinity for the 5-HT$_6$ receptor. The present invention therefore provides, in a first aspect, a compound of formula (I) or a pharmaceutically acceptable salt thereof:

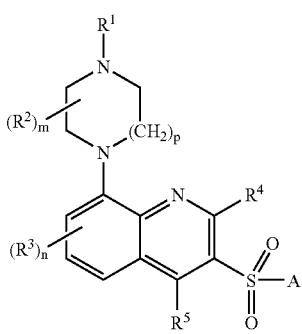

(I)

wherein:
$R^1$ represents —$C_{1-6}$ alkyl substituted by one or more (e.g. 1, 2 or 3) halogen or cyano groups, —$C_{0-4}$ alkyl-$C_{3-8}$cycloalkyl, —$C_{2-4}$ alkyl-oxy-$C_{1-4}$ alkyl, $C_{1-4}$ alkyl-aryl, —$C_{1-4}$ alkyl-heteroaryl or —$C_{0-4}$ alkyl-heterocyclyl;
wherein said cycloalkyl, aryl, heteroaryl or heterocyclyl groups of $R^1$ may be optionally substituted by one or more (e.g. 1, 2 or 3) halogen, $C_{1-6}$ alkyl, $C_{1-6}$ alkoxy, cyano, amino or trifluoromethyl groups;
$R^2$ represents hydrogen or $C_{1-6}$ alkyl;
m represents an integer from 1 to 4, such that when m is an integer greater than 1, two $R^2$ groups may instead be linked to form a $CH_2$, $(CH_2)_2$ or $(CH_2)_3$ group;
$R^3$, $R^4$ and $R^5$ independently represent hydrogen, halogen, cyano, —$CF_3$, —$CF_3O$, $C_{1-6}$ alkyl, $C_{1-6}$ alkoxy, $C_{1-6}$ alkanoyl or a group —$CONR^6R^7$;
$R^6$ and $R_7$ independently represent hydrogen or $C_{1-6}$ alkyl or $R^6$ and $R^7$ together with the nitrogen to which they are attached may form a nitrogen containing heterocyclyl or heteroaryl group;
n represents an integer from 1 to 3;
p represents 1 or 2;
A represents an -aryl, -heteroaryl, -aryl-aryl, -aryl-heteroaryl, -heteroaryl-aryl or -heteroaryl-heteroaryl group;

wherein said aryl and heteroaryl groups of A may be optionally substituted by one or more (e.g. 1, 2 or 3) substituents which may be the same or different, and which are selected from the group consisting of halogen, hydroxy, cyano, nitro, trifluoromethyl, trifluoromethoxy, $C_{1-6}$ alkyl, trifluoromethanesulfonyloxy, pentafluoroethyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, arylsulfonyl, arylsulfonyloxy, arylsulfonyl$C_{1-6}$ alkyl, $C_{1-6}$ alkylsulfonamido, $C_{1-6}$ alkylamido, $C_{1-6}$ alkylsulfonamido$C_{1-6}$ alkyl, $C_{1-6}$ alkylamido$C_{1-6}$ alkyl, arylsulfonamido, arylcarboxamido, arylsulfonamido$C_{1-6}$ alkyl, arylcarboxamido$C_{1-6}$ alkyl, aroyl, aroyl$C_{1-6}$ alkyl, aryl$C_{1-6}$ alkanoyl, or a group $CONR^8R^9$ or $SO_2NR^8R^9$, wherein $R^8$ and $R^9$ independently represent hydrogen or $C_{1-6}$ alkyl or $R^8$ and $R^9$ together with the nitrogen atom to which they are attached may form a nitrogen containing heterocyclyl or heteroaryl group;
or solvates thereof.

Alkyl groups, whether alone or as part of another group, may be straight chain or branched and the groups alkoxy and alkanoyl shall be interpreted similarly. Alkyl moieties are more preferably $C_{1-4}$ alkyl, e.g. methyl or ethyl. The term 'halogen' is used herein to describe, unless otherwise stated, a group selected from fluorine, chlorine, bromine or iodine.

The term "aryl" includes single and fused rings for example, phenyl or naphthyl.

The term "heteroaryl" is intended to mean a 5-7 membered monocyclic aromatic or a fused 8-10 membered bicyclic aromatic ring containing 1 to 3 heteroatoms selected from oxygen, nitrogen and sulfur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include benzofused aromatic rings such as quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like. Heteroaryl groups, as described above, may be linked to the remainder of the molecule via a carbon atom or, when present, a suitable nitrogen atom except where otherwise indicated above.

The term "nitrogen containing heteroaryl" is intended to represent any heteroaryl group as defined above which contains a nitrogen atom.

It will be appreciated that wherein the above mentioned aryl or heteroaryl groups have more than one substituent, said substituents may be linked to form a ring, for example a carboxyl and amine group may be linked to form an amide group.

The term "heterocyclyl" is intended to mean a 4-7 membered monocyclic saturated or partially unsaturated aliphatic ring or a 4-7 membered monocyclic saturated or partially unsaturated aliphatic ring containing 1 to 3 heteroatoms selected from oxygen or nitrogen fused to a benzene or monocyclic heteroaryl ring. Suitable examples of such monocyclic rings include pyrrolidinyl, piperidinyl, piperazinyl, morpholinyl, thiamorpholinyl, diazepanyl, azepanyl, dihydroimidazolyl, tetrahydropyranyl, tetrahydrothiapyranyl and tetrahydrofuranyl. Suitable examples of benzofused heterocyclic rings include dihydroindolyl, dihydroisoindolyl, tetrahydroquinolinyl, tetrahydrobenzazepinyl and tetrahydroisoquinolinyl.

The term "nitrogen containing heterocyclyl" is intended to represent any heterocyclyl group as defined above which contains a nitrogen atom.

Preferably, $R^1$ represents
$C_{1-6}$ alkyl substituted by one or more (e.g. 1, 2 or 3) halogen or cyano groups (e.g. —$CH_2$—$CF_3$ or $CH_2CN$);

—$C_{0-4}$ alkyl-$C_{3-8}$ cycloalkyl (e.g. cyclopropyl, cyclobutyl, cyclopentyl, cyclohexyl or cyclopropylmethyl);

—$C_{2-4}$ alkyl-oxy-$C_{1-4}$ alkyl (e.g. methoxyethyl); or

—$C_{1-4}$ alkyl-aryl (e.g. benzyl) optionally substituted by a halogen (e.g. fluorine) atom.

More preferably, $R^1$ represents —$C_{0-4}$ alkyl-$C_{3-8}$cycloalkyl (e.g. cyclopropyl, cyclobutyl, cyclopentyl, cyclohexyl or cyclopropylmethyl), especially cyclopropylmethyl.

Preferably $R^2$ represents hydrogen or methyl (e.g. 3-methyl). More preferably, $R^2$ represents hydrogen.

Preferably $R^3$ represents hydrogen, methyl (e.g. 6-methyl) or halogen (e.g. 7-chloro).

More preferably, $R^3$ represents hydrogen.

Preferably $R^4$ and $R^5$ independently represent hydrogen or methyl, especially hydrogen.

Preferably n and p both represent 1.

In a preferred embodiment, m represents 1 or 2, most preferably 1.

In another preferred embodiment, m represents 2, and both $R^2$ groups together are linked to form a group ($CH_2$) linking C-2 and C-5 of the piperazine ring.

Preferably, A represents an optionally substituted -aryl, -heteroaryl, -aryl-aryl or -heteroaryl-heteroaryl group.

More preferably, A represents an -aryl (e.g. phenyl) or -heteroaryl (e.g. pyridyl) group optionally substituted by a halogen (e.g. chlorine, fluorine or bromine), cyano, trifluoromethyl or trifluoromethoxy group. Most preferably, A represents unsubstituted phenyl.

Preferred compounds according to the invention include examples E1-E8 as shown below, or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes within its scope all possible stoichiometric and non-stoichiometric forms.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:

(a) reductive alkylation of a compound of formula (II)

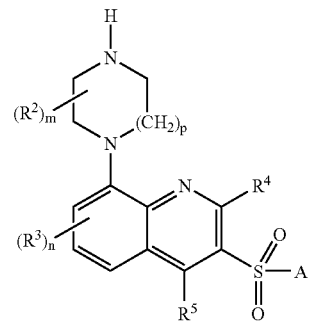

wherein A, $R^2$, $R^3$, $R^4$, $R^5$, m, n and p are as defined above, using an appropriate aldehyde or ketone, wherein said aldehyde or ketone may optionally be generated by hydrolysis of an appropriate precursor e.g. an acetal or ketal; or (b) alkylation of a compound of formula (II) as defined above, using a compound of formula $R^1$-L wherein $R^1$ is as defined above and L is a suitable leaving group such as halogen or a methylsulfonyloxy or 4-tolylsulfonyloxy group;

(c) deprotecting a compound of formula (I) which is protected; and thereafter optionally (d) interconversion to other compounds of formula (I) and/or forming a pharmaceutically acceptable salt and/or solvate.

Process (a) may be typically carried out in the presence of a reducing agent such as sodium cyanoborohydride or sodium triacetoxyborohydride using a solvent such as ethanol, dichloromethane or 1,2-dichloroethane.

Process (b) may be typically carried out in the presence of a base such as triethylamine or diisopropylethylamine using a solvent such as ethanol or isopropanol.

In process (c), examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid. A further amine protecting group includes methyl which may be removed using standard methods for N-dealkylaton (e.g. 1-chloroethyl chloroformate under basic conditions followed by treatment with methanol).

Process (d) may be performed using conventional interconversion procedures such as epimerisation, oxidation, reduction, reductive alkylation, alkylation, nucleophilic or electrophilic aromatic substitution, ester hydrolysis or amide bond formation. Such a process may involve interconversions of the groups $R^3$, $R^4$ and $R^5$, for example. It will be appreciated that such interconversion may be interconversion of protected derivatives of formula (I) which may subsequently be deprotected following interconversion.

Compounds of formula (II) may be prepared in accordance with any one of processes (e), (f) and (g) below:

(e) reacting a compound of formula (III)

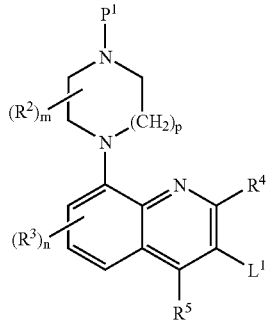

(III)

wherein $R^2$, $R^3$, $R^4$, $R^5$, m, n and p are as defined above, $L^1$ is a leaving group such as iodo or trifluoromethylsulfonyloxy and $P^1$ represents a suitable N-protecting group (such as t-butyloxycarbonyl (Boc), benzyloxycarbonyl or methyl) with a compound of formula A-SO$_2$H, (or A-SH followed by a subsequent oxidation step) wherein A is as defined above and thereafter removing the $P^1$ protecting group as described in process (c) above; or (e) reacting a compound of formula (IV)

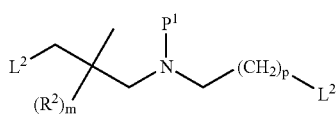

(IV)

with a compound of formula (V)

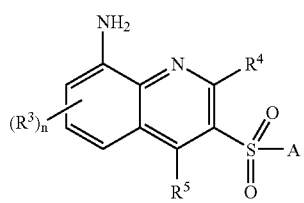

(V)

wherein $P^1$, $R^2$, $R^3$, $R^4$, $R^5$, A, m, n and p are as defined above, and $L^2$ represents a suitable leaving group, such as a halogen atom and thereafter removing the $P^1$ protecting group as described in process (c) above; or (g) reacting a compound of formula (VI)

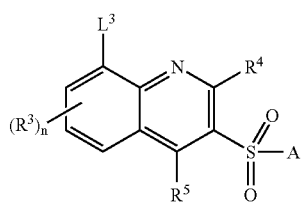

(VI)

with a compound of formula (VII)

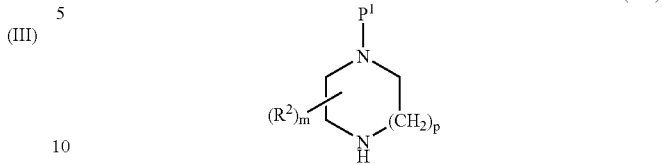

(VII)

wherein $P^1$, $R^2$, $R^3$, $R^4$, $R^5$, m, n, p and A are as defined above and $L^3$ represents a suitable leaving group, such as a halogen atom (e.g. a bromine or iodine atom) or a trifluoromethylsulfonyloxy group, and thereafter removing the $P^1$ protecting group as described in process (c) above.

Process (e) wherein a compound of formula (III) is reacted with a compound of formula A-SO$_2$H typically comprises use of basic conditions and may be most conveniently carried out by using a suitable salt of the compound A-SO$_2$H (e.g. the sodium salt) in an appropriate solvent such as N,N-dimethylformamide, in the presence of a transition metal salt such as copper (I) iodide.

Process (e) wherein a compound of formula (III) is reacted with a compound of formula A-SH typically comprises use of basic conditions e.g. by using a suitable salt of the compound A-SH (e.g. the sodium salt) in an appropriate solvent such as N,N-dimethylformamide, in the presence of a suitable metal salt such as copper (I) iodide, followed by use of a suitable oxidant such as 3-chloroperbenzoic acid, peracetic acid or potassium monopersulfate.

Process (f) may be performed in the presence of a suitable base, such as sodium carbonate and the use of a suitable solvent such as n-butanol.

Process (g) may be performed in the presence of a palladium, nickel or copper catalyst, for example a mixture of a palladium source such as Pd$_2$(dba)$_3$ and a suitable ligand such as (R)-, (S)- or (+)-2,2'-bis(diphenylphosphino)-1,1'-binaphthyl (BINAP) or (2-dicyclohexylphosphanylphenyl)-dimethylamine, or 1,1'-bis-diphenylphosphinoferrocene together with a suitable base such as sodium t-butoxide, in an inert solvent such as 1,4-dioxane.

Compounds of formula (III) may be prepared by reacting a compound of formula (VIII)

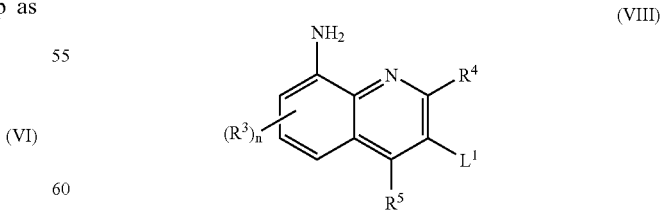

(VIII)

wherein $R^3$, $R^4$, $R^5$, n and $L^1$ are as defined above, with a compound of formula (IV) as defined above. This process typically comprises the use of a suitable base, such as sodium carbonate and the use of a suitable solvent such as n-butanol.

Compounds of formula (V) may be prepared in accordance with the following scheme:

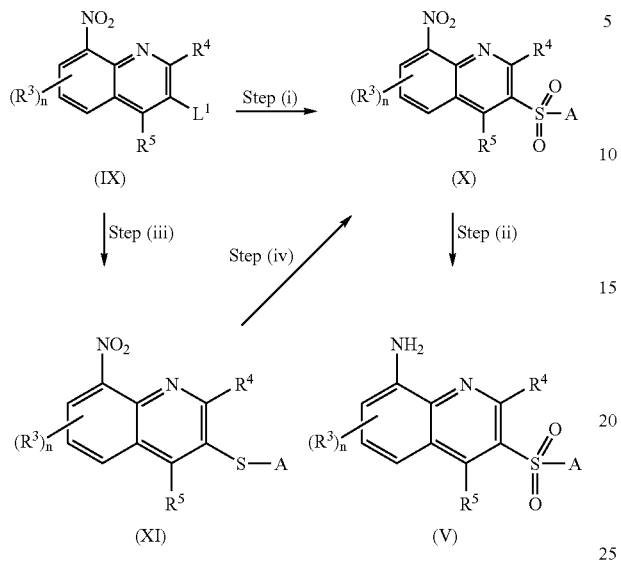

wherein $R^3$, $R^4$, $R^5$, n, A and $L^1$ are as defined above.

Step (i) typically comprises reaction of a compound of formula (IX) with a compound of formula A-SO$_2$-M, wherein A is as defined above and M is a metal residue such as sodium or potassium, in the presence of a copper (I) salt, e.g. copper (I) triflate or copper (I) iodide, in a suitable solvent such as anhydrous N,N-dimethylformamide or 1,4-dioxane, optionally including a ligand such as N,N'-dimethyl-ethylene-1,2-diamine.

Step (ii) typically comprises the use of a suitable reducing agent, for example titanium (III) chloride, or iron powder in an appropriate solvent system, e.g. aqueous tetrahydrofuran and/or acetic acid, respectively.

Alternatively, the transformation shown in step (i) may be carried out using a two step procedure typically comprising steps (iii) and (iv).

Step (iii) typically comprises reaction of a compound of formula (IX) with a compound of formula A-SH, wherein A is as defined above, in the presence of a base such as sodium hydride or potassium phosphate in a suitable solvent such as anhydrous N,N-dimethylformamide or ethylene glycol, optionally in the presence of a copper (I) iodide catalyst.

Step (iv) typically comprises oxidation using a suitable oxidant such as monomagnesium peroxyphthalate, 3-chloroperbenzoic acid, peracetic acid or potassium monopersulfate.

Compounds of formula (VI) wherein $L^3$ represents a halogen atom may be prepared from compounds of formula (V) as defined above according to the following scheme:

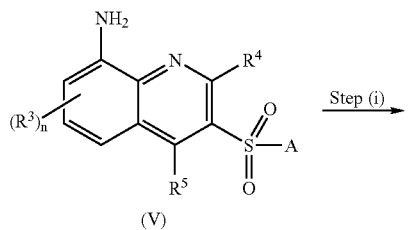

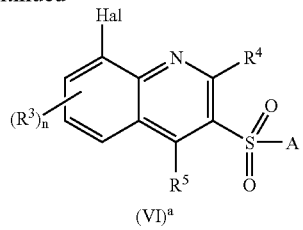

wherein $R^3$, $R^4$, $R^5$, n and A are as defined above and Hal represents a halogen atom.

Step (i) typically comprises diazotisation according to known methods (e.g. using sodium nitrite with aqueous inorganic acid as solvent, or an alkyl nitrite ester using a suitable solvent such as acetonitrile in the presence of anhydrous acid e.g. trifluoroacetic acid), followed by treatment of the resulting diazonium salt with an appropriate halide salt such as copper (I) bromide, potassium iodide or tetrabutylammonium iodide. Such a procedure may be carried out in aqueous solution or using anhydrous conditions, for example using trifluoroacetic acid as solvent.

Alternatively, compounds of formula (VI), wherein $L^3$ represents a halogen atom, may be prepared in accordance with the following procedure:

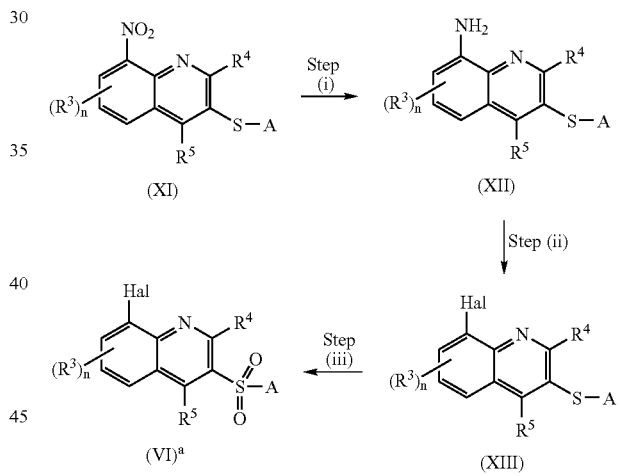

wherein $R^3$, $R^4$, $R^5$, n and A are as defined above and Hal represents a halogen atom.

Step (i) typically comprises a reduction reaction using a suitable reducing agent such as iron powder.

Step (ii) typically comprises diazotisation using an aqueous or non-aqueous source of nitrosonium ions as described above for the preparation of compounds of formula (VI)$^a$ from compounds of formula (V) followed by conversion to a halide.

Step (iii) typically comprises oxidisation using a suitable oxidant such as monomagnesium peroxyphthalate.

Compounds of formula (VI) wherein $L^3$ represents a trifluoromethylsulfonyloxy group may be prepared from compounds of formula (V) as defined above, by diazotisation according to known methods, followed by heating under acidic conditions, followed by treatment with trifluoromethylsulfonic anhydride in the presence of a base, such as pyridine.

Alternatively, compounds of formula (VI) or (XIII) may be prepared from compounds of formula (XIV)

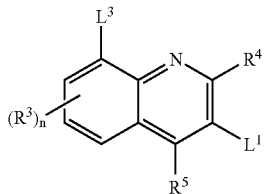

wherein $R^3$, $R^4$, $R^5$, n, $L^1$ and $L^3$ are as defined above, by reaction with compounds of formula A-SO$_2$H or A-SH, respectively wherein A is as defined above, using analogous methods to those described above for process (e). Preferably, $L^1$ and $L^3$ are different, for example $L^1$ and $L^3$ may advantageously represent iodo and chloro, respectively.

Compounds of formula (XIV) as defined above may be prepared from compounds of formula (XV)

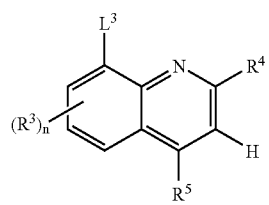

wherein $R^3$, $R^4$, $R^5$, n and $L^3$ are as defined above, using an appropriate halogenating reagent, for example where $L^1$ represents an iodine atom an appropriate process comprises reaction of compound (XV) with N-iodosuccinimide in the presence of acetic acid at elevated temperature, e.g. 80° C. Such a reaction may be advantageously carried out using acetic acid as solvent.

Compounds of formula (XIII) may also be prepared in accordance with the following procedure:

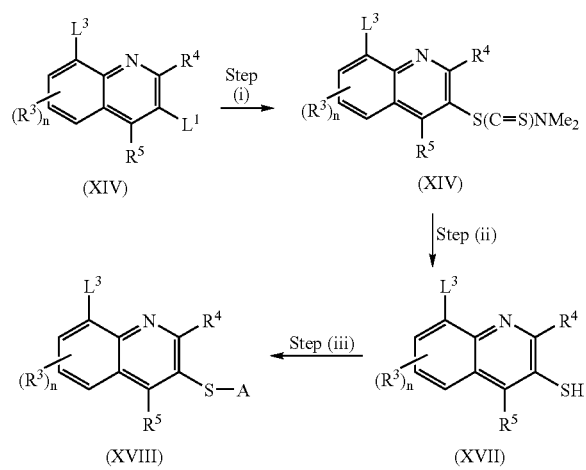

wherein $R^3$, $R^4$, $R^5$, n, $L^1$, $L^3$ and A are as defined above.

Step (i) typically comprises addition of a sulfur nucleophile using a suitable metal salt of dimethyldithiocarbamic acid, e.g. zinc dimethyldithiocarbamate in the presence of a copper (I) salt such as copper triflate and a suitable ligand such as 1,2-dimethylaminoethane in an appropriate solvent such as dimethylsulfoxide at elevated temperature, e.g. 90° C.

Step (ii) comprises cleavage of the thiocarbamoyl moiety using a suitable nucleophile such as sodium sulfide in an appropriate solvent such as aqueous methanol, or trimethylsilanol potassium salt in a suitable solvent such as dimethyl sulfoxide.

Step (iii) typically comprises reaction with a compound of formula A-$L^4$, wherein A is as defined above and $L^4$ represents a leaving group such as halogen, preferably bromine or iodine, in the presence of a copper (I) salt such as copper (I) triflate—benzene complex in a suitable solvent such as dimethyl sulfoxide. Steps (ii) and (iii) may optionally be carried out without isolation of the intermediate thiol of formula (XVII).

Compounds of formula (XI) may be prepared in an analogous manner to those described above for compounds of formula (XIII) starting from compounds of formula (IX) as defined above.

Compounds of formula (IV), (VII), (VIII), (IX) and (XV) are known in the literature or can be prepared by analogous methods.

Pharmaceutically acceptable salts may be prepared conventionally by reaction with the appropriate acid or acid derivative.

Compounds of formula (I) and their pharmaceutically acceptable salts have affinity for the 5-HT$_6$ receptor and are believed to be of potential use in the treatment of certain CNS disorders such as anxiety, depression, epilepsy, obsessive compulsive disorders, migraine, cognitive memory disorders (e.g. Alzheimer's disease, age related cognitive decline and mild cognitive impairment), Parkinson's Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia (in particular cognitive deficits of schizophrenia), stroke and also disorders associated with spinal trauma and/or head injury such as hydrocephalus. Compounds of the invention are also expected to be of use in the treatment of certain GI (gastrointestinal) disorders such as IBS (Irritable Bowel Syndrome). Compounds of the invention are also expected to be of use in the treatment of obesity.

Thus the invention also provides a compound of formula (I) or a pharmaceutically acceptable salt thereof, for use as a therapeutic substance, in particular in the treatment or prophylaxis of the above disorders. In particular the invention provides for a compound of formula (I) or a pharmaceutically acceptable salt thereof, for use in the treatment of depression, anxiety, Alzheimer's disease, age related cognitive decline, ADHD, obesity, mild cognitive impairment, schizophrenia, cognitive deficits in schizophrenia and stroke.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment or prophylaxis of the above disorders.

5-HT$_6$ antagonists have the potential to be capable of increasing basal and learning-induced polysialylated neuron cell frequency in brain regions such as the rat medial temporal lobe and associated hippocampus, as described in WO 03/066056. Thus, according to a further aspect of the present invention, we provide a method of promoting neuronal growth within the central nervous system of a mammal which comprises the step of administering a compound of formula (I) or a pharmaceutically acceptable salt thereof.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Description 1

3-Bromo-8-(4-methyl-piperazin-1-yl)-quinoline (D1)

bis-(2-Chloroethyl)-methyl-amine hydrochloride (3.7 g, 19.2 mmol) and sodium carbonate (9.0 g, 85 mmol) were added to a suspension of 3-bromo-quinolin-8-ylamine (3.9 g, 17.5 mmol) (for synthesis see Gershon et al., *Monatsh. Chem.*, 1991, 122, 935) in n-butanol (70 ml). The stirred suspension was heated at reflux for 72 h. The reaction mixture was cooled to ambient temperature, diluted with dichloromethane (300 ml) and the solution washed with water (300 ml), dried (MgSO$_4$) and concentrated in vacuo to an oil. The oil was purified by chromatography over silica gel eluting with a gradient of methanol/dichloromethane to afford the title compound (D1) as an oil (2.6 g, 8.5 mmol, 49%);

$\delta_H$ (CDCl$_3$) 2.43 (3H, s), 2.78 (4H, br s), 3.44 (4H, br, s), 7.14 (1H, d, J=7.4 Hz), 7.47 (1H, dd, J=7.8 Hz), 8.25 (1H, d, J=2.3 Hz), 8.85 (1H, J=2.3 Hz). Mass Spectrum: C$_{14}$H$_{16}$BrN$_3$ requires 305/307; found 306/308 (MH$^+$).

Description 2

3-Iodo-8-(4-methyl-piperazin-1-yl)-quinoline (D2)

A mixture of 3-bromo-8-(4-methyl-piperazin-1-yl)-quinoline (D1) (1.75 g, 5.7 mmol), copper (I) iodide (5.4 g, 28.5 mmol) and potassium iodide (9.6 g, 57.8 mmol) in hexamethylphosphoramide (20 ml) was heated in an oil bath at 150° C. for 21 h under argon. To the cooled reaction mixture was added toluene (120 ml) and 1M hydrochloric acid (120 ml) and the whole was shaken vigorously for 5 minutes. The insoluble brown solid was then collected by filtration, washed with methanol (3×40 ml) and resuspended in a mixture of dichloromethane (150 ml) and 2M sodium hydroxide (150 ml). After shaking the mixture vigorously, the insoluble material was filtered, washed with dichloromethane (2×50 ml) and discarded. The filtrate and washings were transferred to a separating funnel and the layers were separated. The aqueous phase was extracted with dichloromethane (2×100 ml) and the combined organic extracts were dried (MgSO$_4$) and concentrated to a brown oil (1.5 g) which was identified by NMR spectroscopy as a mixture of the title compound (D2) and 3-bromo-8-(4-methyl-piperazin-1-yl)-quinoline (D1) in a ratio of 4:1. This mixture was used directly in the next stage (see Example 1).

3-Iodo-8-(4-methyl-piperazin-1-yl)-quinoline (D2): $\delta_H$ (CDCl$_3$) 2.41 (3H, s), 2.76 (4H, br s), 3.42 (4H, br s), 7.14 (1H, d, J=6.8 Hz), 7.29 (1H, d, J=7.4 Hz), 7.44 (1H, dd, J=7.8 Hz), 8.47 (1H, d, J=2.3 Hz), 8.98 (1H, d, J=2.3 Hz); Mass Spectrum: C$_{14}$H$_{16}$IN$_3$ requires 353; found 354 (MH$^+$).

Description 3

3-Iodo-8-nitroquinoline (D3)

A stirred mixture of 8-nitroquinoline (100 g, 0.57 mol) in acetic acid (500 ml) was treated with N-iodosuccinimide (155 g, 0.69 mol) portionwise over 10 minutes, and warmed to 62° C. for 6 h. A further portion of N-iodosuccinimide (25 g, 0.14 mol) was introduced and the mixture stirred for a further 16 h before cooling to ambient temperature. The solvent was removed in vacuo, keeping the temperature below 35° C. The residue was dissolved in dichloromethane (2 L) and washed successively with saturated aqueous sodium bicarbonate solution (2×1 L), 10% aqueous sodium thiosulfate solution (1 L), water (1 L), brine (100 ml), then the organic phase was dried over magnesium sulfate. The mixture was filtered and the solvent removed to give a yellow solid which was recrystallised from ethyl acetate to give the title compound (D3) (168 g, 97%) as a yellow solid;

$\delta_H$ (CDCl$_3$) 7.65 (1H, app.t), 7.94 (1H, dd), 8.07 (1H, dd), 8.66 (1H, d, J=2 Hz), 9.19 (1H, d, J=2 Hz); Mass Spectrum: C$_9$H$_5$IN$_2$ requires 300; found 301 (MH$^+$).

Description 4

8-Nitro-3-phenylsulfonylquinoline (D4)

3-Iodo-8-nitroquinoline (D3) (135 g, 0.45 mol), was suspended in dimethylformamide (2.4 L) in a 5 L 3-necked flask fitted with an overhead stirrer, under an argon atmosphere. This mixture was treated successively with anhydrous sodium phenylsulfinate (99.6 g 0.608 mol), and bis-(copper (I) triflate) benzene complex (170 g, 0.338 mol). The resulting slurry was heated to 65° C. for 18 h. The mixture was cooled, filtered and the solvent evaporated in vacuo. Acetone (2.5 L) was added to the residue and the solution filtered. The filtrate was evaporated in vacuo, a further 2.5 L of acetone added and the mixture filtered again. The solvent was evaporated in vacuo and the residue dissolved in chloroform (3 L) and washed with 10% aqueous ammonia (2×2 L), and the organic phase was dried over magnesium sulfate and the solvent evaporated in vacuo. The dark brown residue was purified using a Biotage flash-150 chromatography apparatus (5 kg silica gel) eluting with hexane and increasing proportions of ethyl acetate to give the title compound (D4) (81.5 g, 58%) as a yellow solid;

$\delta_H$ (d6-DMSO) 7.67 (2H, t), 7.57 (1H, d, 7.96 (1H, t), 8.13 (2H, d), 8.51 (1H, d), 8.59 (1H, d), 9.42 (1H, d), 9.50 (1H, d); Mass Spectrum: C$_{15}$H$_{10}$SO$_4$N$_2$ requires 314; found 315 (MH$^+$).

Description 4 (Alternative Procedure)

8-Nitro-3-phenylsulfonylquinoline (D4)

A 2 L vessel was charged with 3-iodo-8-nitroquinoline (D3) (70.8 g, 236 mmol), copper (I) iodide (2.25 g, 11.8 mmol, 5 mol %), potassium phosphate (100 g, 472 mmol, 2 eq), ethylene glycol (0.71L, 10 vol) and benzenethiol (36.2 ml, 354 mmol). The mixture was stirred and heated at 80° C. for 3.5 hours. The reaction mixture was cooled to 20° C. then H$_2$O (700 ml) and dichloromethane (700 ml) were added, the mixture was stirred for 5 minutes then the lower organic layer was removed (contained solids). Charcoal (35.4 g, Norit SX) was added to the organic layer and the mixture was stirred at room temperature for 15 min then filtered through GF/F filter paper. The filter cake was rinsed with dichloromethane (140 ml) and the combined filtrate was washed with H$_2$O (350 ml). The resulting dichloromethane solution was added to a suspension of magnesium monoperoxyphthalic acid hexahydrate (210 g, 424 mmol, 1.8 eq) in a mixture of dichloromethane (700 ml) and methanol (140 ml) over 45 minutes maintaining 18° C.<23° C. The resulting mixture was stirred rapidly for 2.25 hours at 20° C. to 23° C., then 10% w/v aqueous sodium sulfite (700 ml) was added over 15 minutes. the mixture was separated and treated with saturated aqueous sodium bicarbonate (280 ml). The mixture was stirred for 20 min before the layers were allowed to settle. The lower organic layer was removed, washed with water (280 ml), then concentrated at atmospheric pressure to ~210 ml. The resulting mixture was cooled to 0° C., stirred for 2 hrs then filtered. The filter cake was washed with cold (0-5° C.) dichloromethane (70 ml) then dried in vacuo at 25 to 40° C. to give the title compound (D4) as a light yellow solid in 64-66% yield, identical spectroscopically to that prepared by the original D4 method above.

Description 5

8-Amino-3-phenylsulfonylquinoline (D5)

A slurry of 8-nitro-3-phenylsulfonylquinoline (D4) (46.7 g, 172 mmol), in tetrahydrofuran (750 ml) was added to a stirred solution of 30% titanium (III) chloride in aqueous HCl (470 ml) [Supplied by BDH] cooled in an ice bath, at such a rate that the temperature was maintained below 35° C. Once the addition was completed, the solution was stirred for a further 10 minutes then water (1.5 L) was introduced and the mixture poured into a 5 L beaker. The rapidly stirred solution was treated by portionwise addition of solid potassium carbonate in order to attain pH~8.5. EDTA (250 g, 0.86 mol) was added and followed by further potassium carbonate to maintain pH~8.5. The mixture was extracted with dichloromethane (3×1 L) and the combined organic phase passed through a silica plug (500 g) eluting with further dichloromethane (1 L) and 10% ethyl acetate in dichloromethane (1 L). The combined organic phases were evaporated and the residue subjected to purification using Biotage Flash-75 chromatography apparatus (2 kg silica gel), eluting with dichloromethane and increasing proportions of ether to give the title compound (D5) (34.5 g, 72%) as a pale brown solid;

$\delta_H$ (CDCl$_3$) 5.0 (2H, br s), 7.02 (1H, dd), 7.25 (1H, dd), 7.44 (1H, t), 7.50-7.59 (3H, m), 8.00-8.40 (2H, m), 8.70 (1H, s), 0.09 (1H, s); Mass Spectrum: C$_{15}$H$_{12}$SO$_2$N$_2$ requires 284; found 285 (MH$^+$).

Description 6

8-Iodo-3-phenylsulfonylquinoline (D6)

From 8-Amino-3-phenylsulfonylquinoline (D5) trifluoroacetic acid using n-butyl nitrite in acetonitrile followed by tetra-(n-butyl)ammonium iodide.

$\delta_H$ (CDCl$_3$) 7.39 (1H, t), 7.53-7.63 (3H, m), 7.96 (1H, d), 8.04 (2H, dd), 8.50 (1H, dd), 8.79 (1H, d), 9.32 (1H, d); Mass Spectrum: C$_{15}$H$_{10}$NO$_2$SI requires 395; found 396 (MH$^+$).

Description 6 (Alternative Procedure)

8-Iodo-3-phenylsulfonylquinoline (D6)

A solution of sodium nitrite (5.44 g, 78.8 mmol, 1.2 eq) in water (125 ml, 5 vol) was added to a stirred slurry of 8-amino-3-phenylsulfonylquinoline methanesulfonic acid salt (D8) (25.0 g, 65.7 mmol) in 5M HCl (500 ml, 20 vol). The mixture was stirred at 23° to 24.5° C. for 1 hr 5 min then acetonitrile (200 ml, 8 vol) was added. After 10 min a solution of sodium iodide (14.8 g, 98.6 mmol, 1.5 eq) in water (125 ml, 5 vol) was added over 3 min, resulting in the formation of a brown mixture and the evolution of gas. The brown mixture was stirred at 25° C. to 23° C. for 1 hr 5 min then dichloromethane (500 ml, 20 vol) was added and the mixture was stirred for 5 min. The lower organic layer was removed and the aqueous layer was extracted with dichloromethane (125 ml, 5 vol).

The combined organic layers were washed with 10% w/v sodium sulfite (125 ml, 5 vol) then concentrated under reduced pressure. The resulting mixture was filtered and the cake was washed with acetonitrile (2×25 ml) and dried in a 40° C. oven under reduced pressure to afford the title compound D6; yield 15.27 g, 59%, identical spectroscopically to that prepared by the original D6 method above.

Description 7

8-(4-t-Butoxycarbonyl)piperazin-1-yl-3-phenylsulfonylquinoline (D7)

8-Iodo-3-phenylsulfonylquinoline (D6) (25.2 g, 63.6 mmol) was dissolved in dry, de-gassed dioxan (500 ml) under argon. To this solution was added sodium t-butoxide (8.56 g, 89.2 mmol) and 1-t-butyloxycarbonyl piperazine (14.2 g, 76.4 mmol) followed by a suspension of catalyst under argon. The catalyst was prepared by sonication of a mixture of tris-(dibenzylideneacetone)dipalladium(0) (1.75 g, 1.91 mmol) and 2-dicyclohexylphosphino-2'-(N,N-dimethyl amino)biphenyl (2.25 g, 5.73 mmol) in dry degassed dioxane (10 ml) for 2 minutes. This mixture was stirred at 40° C. for 5 h after which a further charge of catalyst was administered (prepared as above on half the scale) and stirring continued for 16 h at 40° C.

The mixture was filtered and the solvent removed. The residue was adsorbed onto silica and chromatographed on silica eluting with 1% methanol in dichloromethane to give the title compound (D7) (22.0 g, 76%) as a yellow solid;

$\delta_H$ (CDCl$_3$) 1.49 (9H, t), 3.31 (4H, m) 3.72 (4H, m), 7.25 (1H, m), 7.52 (2H, t) 7.57 (3H, m) 8.00 (2H, m) 8.76 (1H, d) 9.21 (1H, d); Mass Spectrum: C$_{24}$H$_{27}$N$_3$O$_4$S requires 453; found 454 (MH$^+$).

Description 8

8-Amino-3-phenylsulfonylquinoline methanesulfonic acid salt (D8)

A suspension of iron powder (26.7 g, 5 eq, 325 mesh) in THF (300 ml, 10 vol), water (30 ml, 1 vol) and acetic acid (19.2 ml, 3.5 eq) was heated to 50° C. 8-Nitro-3-phenylsulfonylquinoline (D4) (30 g, 1 wt) was added portionwise to the mixture over 30 min, keeping the temperature below 60° C. The reaction mixture was stirred at 50 to 55° C. for 60 min. Toluene (240 ml, 8 vol) was added, followed by water (60 ml, 2 vol) before cooling to 40° C. and filtering the mixture through a silica gel plug. The silica plug was washed with toluene (2×60 ml, 2 vol). The layers of the combined filtrate were separated and the organic layer concentrated in vacuo to ca 10 volumes. The reaction mixture was warmed to 77° C. then treated with methanesulfonic acid (7.42 ml, 1.2 eq) added over 15 min maintaining the temperature at 75 to 80° C. The resulting orange suspension was cooled slowly to ambient, stirred at ambient temperature for ca 2 h, then the product filtered and washed with toluene (3×60 ml). The resulting pink solid (D8) was dried in vacuo at ca 45° C. to constant weight. Yield: 34.17 g, 94%.

$\delta_H$ (d6-DMSO) 2.46 (3H, s), 7.54 (1H, d, J=8 Hz), 7.60-7.70 (3H,m), 7.70-7.75 (1H, t, J=8 Hz), 7.81 (1H, J=8 Hz), 8.13 (2H, d, J=8 hz), 8.28 (3H, bs), 9.14 (1H, d, J=2 Hz), and 9.28 (1H, J=2 Hz).

Description 9

8-(4-Methyl-piperazin-1-yl)-3-phenylsulfonylquinoline (D9)

A 4:1 mixture of 3-iodo-8-(4-methyl-piperazin-1-yl)-quinoline (D2) and 3-bromo-8-(4-methyl-piperazin-1-yl)-quinoline (D1) (1.5 g), phenylsulfinic acid sodium salt dihydrate (2.52 g, 12.6 mmol) and copper (I) iodide (2.4 g, 12.6 mmol) in N,N-dimethylformamide (25 ml) was stirred in an oil bath at 120° C. for 40 h under argon. To the reaction mixture, cooled to ambient temperature, was added 5% sodium hydrogen carbonate solution (100 ml) and dichloromethane (100 ml) with vigorous shaking. The insoluble material was filtered, washed with dichloromethane (3×20 ml) and discarded. The filtrate and washings were transferred to a separating funnel and the layers separated. The aqueous layer was extracted with dichloromethane (100 ml) and the combined organic extracts were washed with water (100 ml), dried (MgSO$_4$) and concentrated in vacuo to an oil (0.9 g). The oil was purified by chromatography over silica gel eluting with a gradient of methanol/dichloromethane to afford an orange oil (0.28 g, Rf 0.11, methanol/dichloromethane 1:19). This material was further purified by passage through a strong cation exchange (SCX) column eluting firstly with methanol (fractions discarded) and then with methanol/aqueous ammonia-880 (10:1) to give the title compound (D9) as an orange oil (0.152 g, 0.41 mmol, 7% over two steps);

$\delta_H$ (CDCl$_3$) 2.40 (3H, s), 2.72-2.76 (4H, m), 3.44 (4H, br, s), 7.25-7.27 (1H, m), 7.48-7.61 (5H, m), 7.99-8.02 (2H, m), 8.75 (1H, d, J=2.4 Hz), 9.21 (1H, d, J=2.4 Hz); Mass Spectrum: C$_{20}$H$_{21}$N$_3$O$_2$S requires 367; found 368 (MH$^+$).

Description 10

8-(4-Methyl-piperazin-1-yl)-3-phenylsulfonylquinoline hydrochloride(D10)

A solution of 8-amino-3-phenylsulfonylquinoline (D5) (38.8 g, 137 mmol) in n-butanol (360 ml) was treated with bis-(2-chloroethyl)-methyl-amine hydrochloride (40 g, 138 mmol) and sodium carbonate (72 g, 0.68 mol). The mixture was heated to a vigorous reflux (~100° C.) for 16 h then a further portion of bis-(2-chloroethyl)-methyl-amine hydrochloride (25 g, 86 mmol) introduced and heating continued for a further 4 h. The solution was cooled and a 1:1 mixture of saturated aqueous sodium bicarbonate and aqueous 10% sodium thiosulphate solution (2 L) added. Stirring was continued at ambient temperature for 16 h then the aqueous phase was extracted with dichloromethane (3×500 ml), the combined organic phase dried over magnesium sulphate, evaporated in vacuo and subjected to chromatography on a Biotage Flash 75 apparatus (1 kg Silica gel) to afford the free base form of the title compound (11.6 g), identical spectroscopically to that prepared by D$_9$. A portion of this material was treated with 1M HCl in ether then evaporated to afford the hydrochloride salt (D10) as a yellow solid;

$\delta_H$ (CDCl$_3$) 2.95 (3H, d), 2.38-3.52 (4H, m), 4.01-4.06 (2H, m), 4.19-4.26 (2H, m), 7.60 (2H, t), 7.70 (1H, t), 7.96 (1H, t), 8.07 (2H, s), 8.09 (2H, s), 9.34 (1H, d), 9.63 (1H, d), 12.9 (1H, br s).

Description 11

3-Phenylsulfonyl-8-piperazin-1-yl-quinoline hydrochloride (D11)

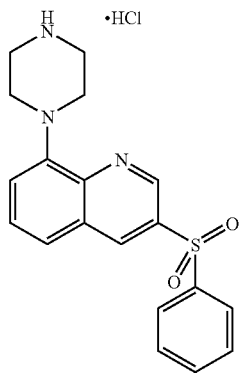

A stirred solution of 8-(4-methyl-piperazin-1-yl)-3-phenylsulfonylquinoline hydrochloride (D10) (0.148 g, 0.4 mmol), 1-chloroethyl chloroformate (0.093 ml, 0.85 mmol) and N,N-diisopropylethylamine (0.148 ml, 0.85 mmol) in 1,2-dichloroethane (9 ml) was heated at reflux for 1.25 h under argon. The reaction mixture was cooled to ambient temperature and concentrated in vacuo to an oil. The oil was purified by chromatography over silica gel eluting with a gradient of methanol/dichloromethane, pooling fractions which contained the major component (Rf 0.9, methanol/dichloromethane 1:19). The purified material was redissolved in methanol (15 ml) and the solution was refluxed for 1 h under argon. The reaction mixture was cooled to ambient temperature and concentrated in vacuo to a solid which was stirred with diethyl ether (5 ml) and filtered to afford the title compound (D11) (0.08 g, 0.21 mmol, 51%);

$\delta_H$(d$_6$-DMSO) 3.32 (4H, br s), 3.55 (4H, br s), 7.35 (1H, d, J=6.5 Hz), 7.63-7.77 (4H, m), 7.86 (1H, d, J=7.4 Hz), 8.10 (2H, m), 9.10 (1H, d, J=2.4 Hz), 9.21 (2H, s), 9.24 (1H, d, J=2.4 Hz); Mass Spectrum: C$_{19}$H$_{19}$N$_3$O$_2$S requires 353; found 354 (MH$^+$).

Description 11 (Alternative Procedure)

3-Phenylsulfonyl-8-piperazin-1-yl-quinoline hydrochloride (D11)

A mixture of 8-(4-t-butoxycarbonyl)piperazin-1-yl-3-phenylsulfonylquinoline (D7), 1,4-dioxane and 4 M aqueous HCl, was stirred at ambient temperature for two hours, then the solvent evaporated. The residue was co-evaporated several times from toluene and the remainder crystallised from hot ethanol to give the title compound (D11) as a yellow crystalline solid;

$\delta_H$(d$_6$-DMSO) 3.32 (4H, br s), 3.55 (4H, br s), 7.35 (1H, d, J 6.5Hz). 7.63-7.77 (4H, m), 7.86 (1H, d, J=7.4 Hz), 8.10 (2H, m), 9.10 (1H, d, J=2.4 Hz), 9.21 (2H, s), 9.24 (1H, d, J=2.4 Hz); Mass Spectrum:C$_{19}$H$_{19}$N$_3$O$_2$S requires 353; found 354 (MH$^+$); m.p. 200° C. (phase change), 270-274° C. (decomposed)

Description 12

3-Phenylsulfonyl-8-piperazin-1-yl-quinoline (D12)

A 100 ml three necked flask was charged with Pd$_2$(dba)$_3$ (174 mg, 0.19 mmol, 0.03 eq), 8-iodo-3-phenylsulfonylquinoline (D6) (2.5 g, 6.33 mmol), 1,1'-bis-diphenylphosphenoferrocene (316 mg, 0.57 mmol), sodium tertbutoxide (851 mg, 8.86 mmol, 1.4 eq) and piperazine (2.72 g, 31.6 mmol, 5 eq). The flask was evacuated and filled with nitrogen 4 times then anhydrous 1,4-dioxane (17.5 ml, 7 vol) was added. The mixture was stirred and heated to 40° C. for 16½ hrs.

The dark solution was allowed to cool to room temperature, dichloromethane (12.5 ml) was added and the solution was washed with H$_2$O (12.5 ml). The aqueous wash was extracted with dichloromethane and the combined organic layers were extracted with 5M HCl (2×12.5 ml). The combined aqueous layers were washed with (dichloromethane 2.5 ml) then transferred to a conical flask, dichloromethane (12.5 ml) was added and the flask was cooled in an ice/water bath. 10M Aqueous sodium hydroxide (13 ml) was added whilst stirring, the mixture was then stirred at room temperature until all the solids were dissolved. The lower organic layer was removed and the aqueous layer was extracted with dichloromethane (7.5 ml), the combined organic layers were concentrated under reduce pressure to ~5 ml. Isooctane (2.5 ml) was added to the dark brown solution resulting in crystallisation, the mixture was stirred at room temp for 5 min then isooctane (22.5 ml) was added over 5 min. The mixture was aged at room temp for 1½ hrs before being cooled in an ice/water bath for 30 min, the mixture was filtered and the cake washed with isooctane (5 ml). The cake was dried under reduced pressure to give the title compound (D12) yield 1.67 g, 75%. Recrystallisation from isopropanol (12 vols) gives material of mp 164° C. in 80% recovery;

$\delta_H$(CDCl$_3$): 1.6 (1H, bs), 3.18 (4H, m), 3.34 (4H, m), 7.27 (1H, m), 7.49-7.60 (5H, m), 8.01 (2H, dd), 8.75, (1H, d), 9.21 (1H, d).

EXAMPLE 1

8-(4-(4-Fluorobenzyl)-piperazin-1-yl)-3-phenylsulfonylquinoline hydrochloride (E1)

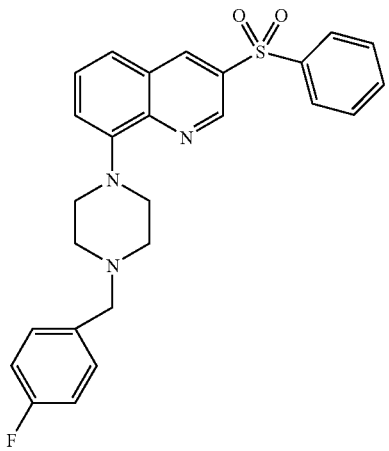

A suspension of 3-phenylsulfonyl-8-piperazin-1-yl-quinoline (D12) (200 mg, 0.55 mmol) in ethanol (4 ml) was treated successively with acetic acid (100 μl), 4-fluorobenzaldehyde (124 mg, 1 mmol) and resin bound Amberlyst cyanoborohydride (~3 mmol/g, 0.5 g). The mixture was stirred at ambient temperature for 18 hours then filtered and the filtrate absorbed onto an SCX cartridge. This was washed with ethanol then eluted with a solution of 3% ammonia in 7% aqueous methanol. The solution was evaporated and the residue subjected to purification by flash chromatography on silica gel (eluting with dichloromethane-methanol-aq. $NH_3$) to give the free base of the title compound:

$\delta_H$ (CDCl$_3$): 2.73-2.77 (4H, m), 3.40 (4H, br.s), 3.59 (2H, s), 7.02 (2H, t), 7.23-7.36 (3H, m), 7.47-7.47 (5H, m), 8.01 (2H, dd), 8.75 (1H, d), 9.20 (1 h, d).

This was treated with 1M HCl in ether then crystallised from isopropanol to give the title compound (E1) as a yellow solid:

Mass Spectrum: $C_{26}H_{24}FN_3O_2S$ requires 461; found 462 (MH$^+$).

EXAMPLE 2

8-(4-Cyclopropylmethyl-piperazin-1-yl)-3-phenyl-sulfonylquinoline hydrochloride (E2)

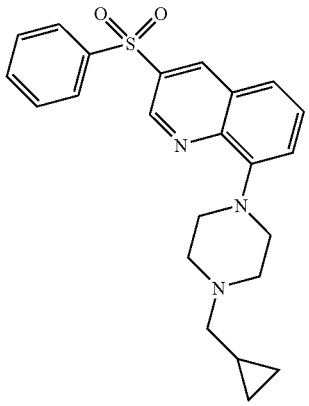

Prepared by the method of Example 1 but using cyclopropylcarboxaldehyde (1 mmol) in place of 4-fluorobenzaldehyde.

Mass Spectrum: $C_{23}H_{25}N_3O_2S$ requires 407; found 408 (MH$^+$).

EXAMPLE 3

8-(4-(Cyclohexyl)-piperazin-1-yl)-3-phenylsulfonylquinoline hydrochloride (E3)

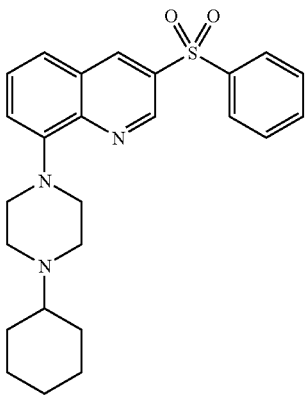

Prepared by the method of Example 1 but using cyclohexanone (1 mmol) in place of 4-fluorobenzaldehyde and heating the mixture to 50° C. for 4 h prior to stirring for 14 h at RT.

$\delta_H$ (CDCl$_3$): 1.31-1.43 (2H, m), 1.60-1.75 (4H, m), 1.99 (2H, br.d), 2.44 (2H, br.d), 3.15 (1H, dt), 3.40-3.50 (4H, m), 4.20-4.36 (4H, m), 7.59 (2H, t), 7.68 (1H, t), 7.91 (1H, t), 8.02-8.14 (4H, m), 9.25 (1H, s), 9.60 (1 h, s), 12.4 (1H, br.s).

Mass Spectrum: $C_{25}H_{29}N_3O_2S$ requires 435; found 436 (MH$^+$).

EXAMPLE 4

8-(4-Cyclopentyl-piperazin-1-yl)-3-phenylsulfonylquinoline hydrochloride (E4)

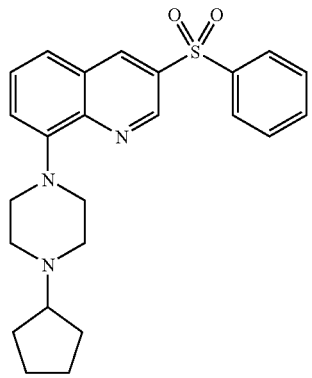

Prepared by the method of Example 3 but using cyclopentanone (1 mmol) in place of cyclohexanone.

Mass Spectrum: $C_{24}H_{27}N_3O_2S$ requires 421; found 422 (MH$^+$).

EXAMPLE 5

8-(4-Cyclobutyl-piperazin-1-yl)-3-phenylsulfonylquinoline hydrochloride (E5)

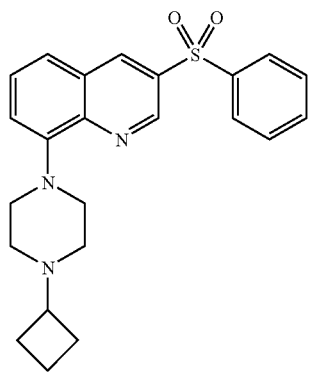

Prepared by the method of Example 3 but using cyclobutanone (1 mmol) in place of cyclohexanone.

Mass Spectrum: $C_{23}H_{25}N_3O_2S$ requires 407; found 408 (MH$^+$).

EXAMPLE 6

8-(4-Cyclopropyl-piperazin-1-yl)-3-phenylsulfonylquinoline hydrochloride (E6)

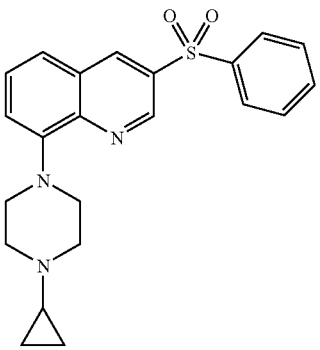

Prepared by the method of Example 3 but using {[1-(ethyloxy)cyclopropyl]oxy}(trimethyl)silane (348 mg, 2 mmol) in place of cyclohexanone and an additional 0.2 ml of acetic acid.

Mass Spectrum: $C_{22}H_{23}N_3O_2S$ requires 393; found 394 (MH+).

EXAMPLE 7

8-(4-(2-methoxyethyl)-piperazin-1-yl)-3-phenylsulfonylquinoline hydrochloride (E7)

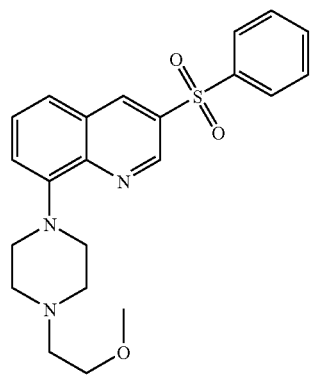

A mixture of 1,1,2-tris-(methoxy)ethane (250 mg, 2.1 mmol), trifluoroacetic acid (0.2 ml), and water (0.2 ml) was warmed to 50° C. for 5 minutes to give a clear solution. The mixture was cooled, and ethanol (2 ml) added followed by Amberlyst hydroxide resin, until neutral pH was reached. This mixture was used in place of cyclohexanone in the method of Example 3, to afford the title compound (E7):

Mass Spectrum: $C_{22}H_{25}N_3O_3S$ requires 411; found 412 (MH+).

EXAMPLE 8

8-(4-(2,2,2-Trifluoroethyl)-piperazin-1-yl)-3-phenylsulfonylquinoline (E8)

A solution of 3-phenylsulfonyl-8-piperazin-1-yl-quinoline (D12) (200 mg, 0.55 mmol) in dry THF (2 ml) was treated with sodium hydride (24 mg, 0.6 mmol, 60% oil dispersion), and 1-bromo-2,2,2-trifluoroethane (815 mg, 5 mmol). The mixture was heated to 100° C. for 4 days then cooled, evaporated and the residue subjected to purification by flash chromatography on silica gel (eluting with dichloromethane-methanol-aq. NH₃) to give the free base form of the title compound. This was treated with 1M HCl in ether then crystallised from isopropanol to give the title compound (E8) as a yellow solid:

Mass Spectrum: $C_{21}H_{20}F_3N_3O_2S$ requires 435; found 436 (MH+).

Pharmacological Data

Compounds can be tested following the procedures outlined in WO98/27081. The compounds of Examples E1-E8 were tested and showed affinity for the 5-HT₆ receptor, having pKi values >7.0 at human cloned 5-HT₆ receptors.

The invention is claimed is:

1. A compound of formula (I):

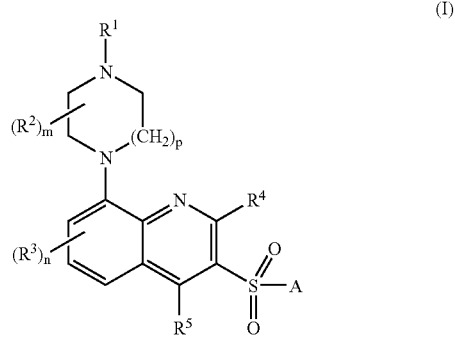

wherein:
R¹ represents —$C_{1-6}$ alkyl substituted by 1, 2, or 3 halogen or cyano groups; —$C_{0-4}$ alkyl-$C_{3-8}$cycloalkyl; —$C_{2-4}$ alkyl-oxy-$C_{1-4}$ alkyl; —$C_{1-4}$ alkyl-aryl, wherein said cycloalkyl or aryl groups of R¹ may be optionally substituted by 1, 2, or 3 groups selected from halogen, $C_{1-6}$ alkyl, $C_{1-6}$ alkoxy, cyano, amino and trifluoromethyl;
R² represents hydrogen or $C_{1-6}$ alkyl;
m represents 1;
R³ represents hydrogen, methyl or halogen;
R⁴ and R⁵ independently represent hydrogen or methyl;
n represents 1;
p represents 1 or 2;
A represents phenyl optionally substituted by a halogen, cyano, trifluoromethyl, or trifluoromethoxy group;
or a pharmaceutically acceptable salt thereof, or a hydrate thereof.

2. The compound according to claim 1, wherein: A is unsubstituted phenyl.

3. A compound which is:
8-(4-(4-Fluorobenzyl)-piperazin-1-yl)-3-phenylsulfonylquinoline;
8-(4-Cyclopropylmethyl-piperazin-1-yl)-3-phenylsulfonylquinoline;
8-(4-(Cyclohexyl)-piperazin-1-yl)-3-phenylsulfonylquinoline;
8-(4-Cyclopentyl-piperazin-1-yl)-3-phenylsulfonylquinoline;
8-(4-Cyclobutyl-piperazin-1-yl)-3-phenylsulfonylquinoline;
8-(4-Cyclopropyl-piperazin-1-yl)-3-phenylsulfonylquinoline;
8-(4-(2-methoxyethyl)-piperazin-1-yl)-3-phenylsulfonylquinoline;
8-(4-(2,2,2-Trifluoroethyl)-piperazin-1-yl)-3-phenylsulfonylquinoline;
or a pharmaceutically acceptable salt thereof, or a hydrate thereof.

4. A pharmaceutical composition which comprises the compound, salt, or hydrate according to claim 1 and a pharmaceutically acceptable carrier or excipient.

5. A pharmaceutical composition which comprises the compound, salt, or hydrate according to claim 3 and a pharmaceutically acceptable carrier or excipient.

6. A method of treating a cognitive memory disorder which comprises administering a therapeutically effective amount of the compound, salt, or hydrate according to claim 1 to a patient in need thereof, wherein the cognitive memory disorder is selected from age related cognitive decline, mild cognitive impairment, and cognitive deficits in schizophrenia.

7. A method of treating a cognitive memory disorder which comprises administering a therapeutically effective amount of the compound, salt, or hydrate according to claim 3 to a patient in need thereof, wherein the cognitive memory disorder is selected from age related cognitive decline, mild cognitive impairment, and cognitive deficits in schizophrenia.

8. A method of treating depression or anxiety which comprises administering to a patient in need thereof a therapeutically effective amount of the compound, salt, or hydrate according to claim 1.

9. A method of treating depression or anxiety which comprises administering to a patient in need thereof a therapeutically effective amount of the compound, salt, or hydrate according to claim 3.

10. A method of treating obesity which comprises administering to a patient in need thereof a therapeutically effective amount of the compound, salt, or hydrate according to claim 1.

11. A method of treating obesity which comprises administering to a patient in need thereof a therapeutically effective amount of the compound, salt, or hydrate according to claim 3.

12. A method of treating Alzheimers disease which comprises administering to a patient in need thereof a therapeutically effective amount of the compound, salt, or hydrate according to claim 1.

13. A method of treating Alzheimers disease which comprises administering to a patient in need thereof a therapeutically effective amount of the compound, salt, or hydrate according to claim 3.

\* \* \* \* \*

UNITED STATES PATENT AND TRADEMARK OFFICE
CERTIFICATE OF CORRECTION

PATENT NO. : 7,439,244 B2 Page 1 of 1
APPLICATION NO. : 10/571405
DATED : October 21, 2008
INVENTOR(S) : Christopher Norbert Johnson and David R. Witty It is certified that error appears in the above-identified patent and that said Letters Patent is hereby corrected as shown below:

Title Page, Item (54)

Title of the Patent should read "Quinoline Compounds and Pharmaceutical Compositions Containing Them"

Signed and Sealed this

Tenth Day of February, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,439,244 B2 | Page 1 of 1 |
| APPLICATION NO. | : 10/571405 | |
| DATED | : October 21, 2008 | |
| INVENTOR(S) | : Christopher Norbert Johnson and David R. Witty | |

It is certified that error appears in the above-identified patent and that said Letters Patent is hereby corrected as shown below:

Title Page, Item (54) and Column 1, lines 1-3

Title of the Patent should read "Quinoline Compounds and Pharmaceutical Compositions Containing Them"

This certificate supersedes the Certificate of Correction issued February 10, 2009.

Signed and Sealed this

Tenth Day of March, 2009

JOHN DOLL
*Acting Director of the United States Patent and Trademark Office*